US00PP18825P2

(12) United States Plant Patent
Griggs

(10) Patent No.: US PP18,825 P2
(45) Date of Patent: May 20, 2008

(54) CHERRY TREE NAMED 'MG 200'

(50) Latin Name: *Prunus avium L.*
Varietal Denomination: MG 200

(76) Inventor: Marcus J. Griggs, 50 Griggs La., Orondo, WA (US) 98843

( * ) Notice: Subject to any disclaimer, the term of this patent is extended or adjusted under 35 U.S.C. 154(b) by 3 days.

(21) Appl. No.: 11/599,198

(22) Filed: Nov. 13, 2006

(51) Int. Cl.
*A01H 5/00* (2006.01)

(52) U.S. Cl. ..... Plt./181
(58) Field of Classification Search ..... Plt./181
See application file for complete search history.

(56) References Cited

U.S. PATENT DOCUMENTS

PP8,954 P * 10/1994 Gruppe et al. ..... Plt./183
PP9,622 P * 8/1996 Gruppe et al. ..... Plt./183
PP13,951 P2 * 7/2003 Doty ..... Plt./181

* cited by examiner

*Primary Examiner*—Wendy C. Haas
(74) *Attorney, Agent, or Firm*—Wells St. John P.S.

(57) ABSTRACT

A new and distinct variety of cherry tree is described and which bears fruit having a red overcolor covering about 80% to 100% of the surface area and a yellow-orange under color, and a mid-season date of ripening which is about 4 days earlier than the 'Rainier' and 'Early Robin' cherry trees when grown under the conditions prevailing in Central Washington.

3 Drawing Sheets

Genus and Species of the Claimed Variety: *Prunus avium* L.
Variety Name: 'MG 200'.

BACKGROUND OF THE NEW VARIETY

The present invention relates to a new and distinct variety of cherry tree '*Prunus avium* L', and which has been denominated varietally as MG 200, and more specifically to a cherry tree which matures for harvesting and shipment during the mid-season under the environmental conditions prevailing in Central Washington state.

DISCOVERY AND ASEXUAL REPRODUCTION

The present variety of cherry tree was discovered as a whole tree mutation growing within a block of 'Rainer' cherry trees (unpatented), and which were planted in 1998. This block of 'Rainer' cherry trees had been planted on 'Geisla 6' rootstock (U.S. Plant Pat. No. 8,954). The discovery of the whole tree mutation occurred during the 2001 growing season when the inventor observed that the present tree produced fruit which was different from the neighboring 'Rainier' cherry trees (unpatented). The inventor, upon identifying the promising new variety, asexually reproduced the new variety during the dormant season between the years 2001 and 2002 by removing budwood from the promising chance mutation and grafting it into trees then growing on 'Geisla 5' and 'Geisla 6' rootstock (U.S. Plant Pat. Nos. 9,622 and 8,954, respectively), and which were growing in an adjacent block. These asexually reproduced trees later bore fruit and the inventor has carefully compared the asexually reproduced trees with that of the original chance mutation including the fruit produced by the respective trees. These subsequent evaluations has confirmed that the trees and fruit produced from these asexual reproductions are identical in all respects to the original chance mutation.

SUMMARY OF THE VARIETY

The 'MG 200' cherry tree is characterized principally as to novelty to producing cherries which are relatively large in size, and have a red overcolor which covers about 80% to about 100% of the fruit surface area. The fruit of the present variety further displays a yellow-orange undercolor. The present variety of cherry tree also produces fruit which are mature for harvesting and shipment about 4 days ahead of the 'Rainer' variety of cherry tree (unpatented); and the 'Early Robin' cherry tree variety (U.S. Plant Pat. No. 13,951) of which it is most closely similar.

The present variety of cherry tree has been compared and contrasted to the adjacent 'Rainer' cherry trees of the same age, and to the 'Early Robin' cherry trees growing in a nearby orchard. The new variety of cherry tree is somewhat similar to the adjacent 'Rainier' cherry trees with respect to its wood, leaf, bloom, fruit flavor, fruit storage life, and bud and bloom cold hardiness. However, the 'MG 200' cherry tree can be distinguished from the adjacent 'Rainier' cherry trees in view of its earlier harvesting date, fruit coloring pattern, fruit size, fruit firmness, pit flesh adherence, sweetness and overall crop yields. Still further, in relative comparison to the adjacent 'Rainer' cherry trees, the branching habit of the trellised, trained trees of the new variety 'MG 200' appears to be more drooping than that displayed by the 'Rainier' cherry trees which are growing nearby. Other characteristics which contrast the present new variety with the adjacent 'Rainier' cherry trees which are growing nearby are set forth in the paragraphs which follow.

BRIEF DESCRIPTION OF THE DRAWINGS

The accompanying drawings are color photographs of various aspects of the present cherry tree. The colors are as nearly true as reasonably possible in color representations of this type. Due to chemical development, processing and printing the leaves and fruit of the present tree may or may not be accurate when compared with the actual specimen.

For this reason, future color references should be made to the color plates provided by The Royal Horticulture Society Colour Chart (3rd Edition) provided by the Royal Horticulture Society of Great Britain.

DETAILED DESCRIPTION

Figure 1:
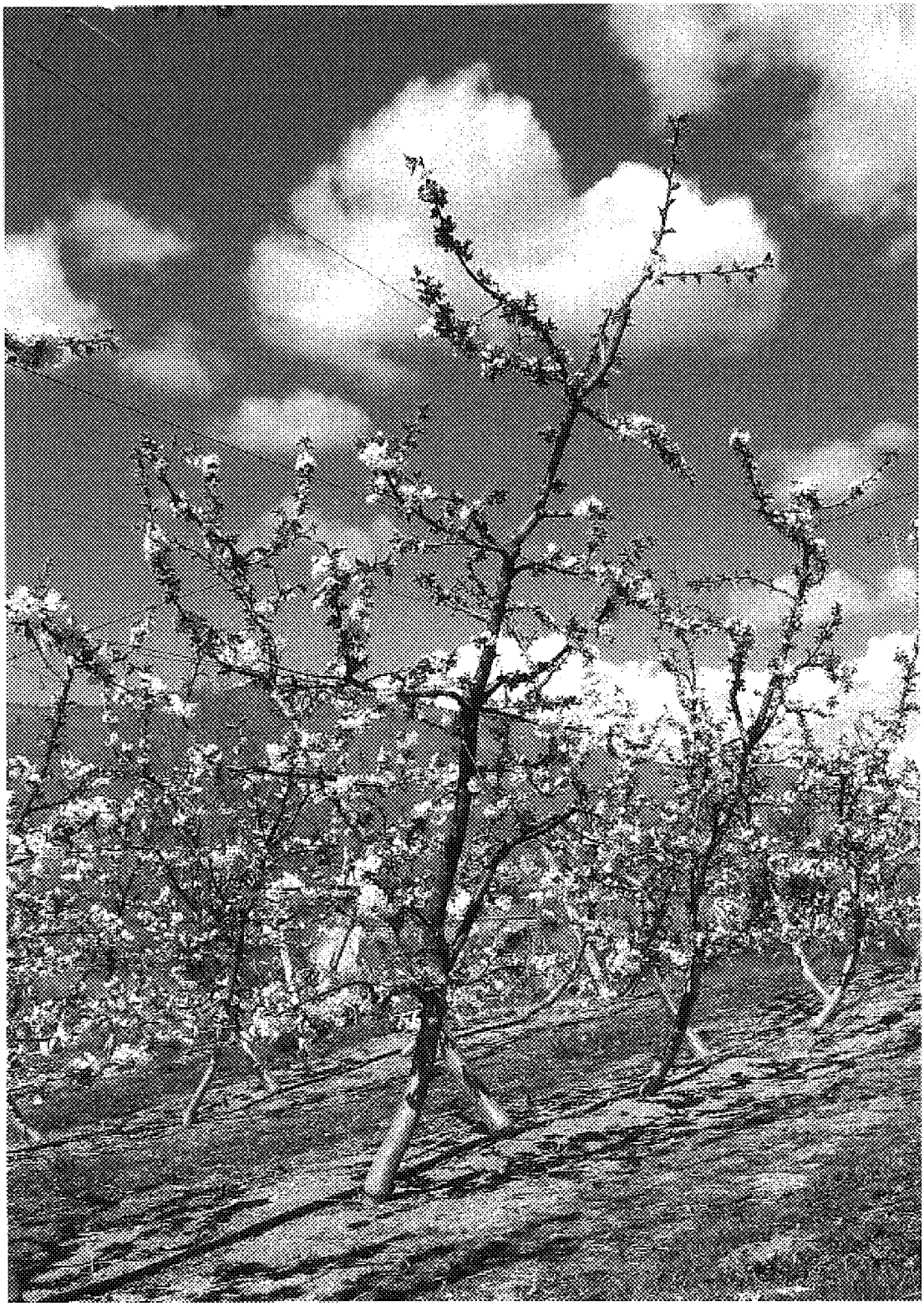
FIG. 1 depicts an 8 year old 'MG 200' cherry tree in bloom as it is trained to an existing trellis system.
Figure 2:
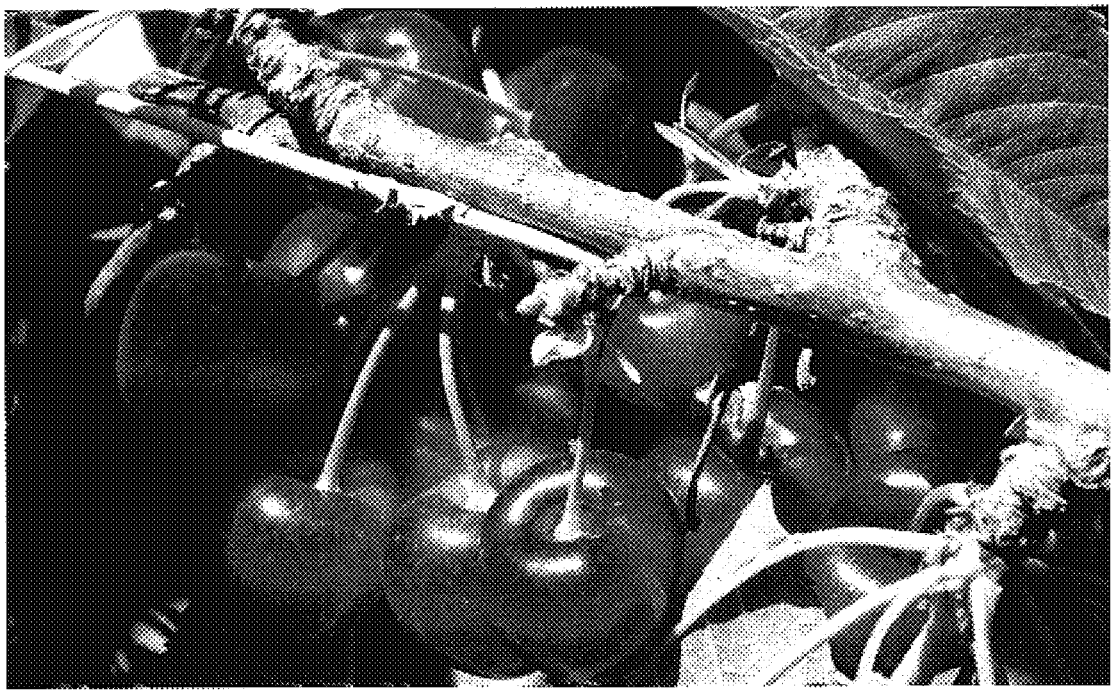
FIG. 2 depicts a typical fruiting branch of the new variety at harvest maturity.

Referring more specifically to the horticultural details of this new and distinct variety of cherry tree, the following characteristics have been observed under the ecological conditions prevailing at the orchard of origin which is located near Orondo, Wash. As indicated, above, all major color code designations are by reference to the Royal Horticulture Society of Great Britain. Common color names are also used occasionally.

TREE

*Size.*—Generally — Considered medium to medium large when grown on the dwarfing 'Geisla 6' rootstock (U.S. Plant Pat. No. 8,954). The present tree expresses many of the same growth characteristics as the surrounding 'Rainer' cherry trees which are also growing on 'Geisla 6' rootstock.

*Vigor.*—Moderately vigorous and similar to the 'Rainer' cherry tree (unpatented), when grown under similar ecological conditions. Average shoot growth expressed on 9 year old trees was about 39.8 cm. when measured at the time of harvest.

*Branching habit.*—When the present variety is trained to a horizontal wire trellis, the branches of the present variety originate substantially in all orientations. The branches of the present variety appear to droop down more than those of the adjacent and similarly trained 'Rainer' cherry trees (unpatented).

*Density.*—Considered moderate for the species. The present variety forms many spurs. The spur development appears similar to the adjacent 'Rainer' cherry trees.

*Tree form.*—Considered to be round headed.

*Hardiness.*—Considered hardy under the prevailing ecological conditions. The variety appears to have a hardiness equal to the 'Rainer' cherry tree when grown in Central Washington.

*Productivity.*—Generally — During the 2006 growing season, the 'MG 200' cherry tree had an average yield of about 35 pounds of cherries per tree. In relative comparison to the adjacent 'Rainer' cherry trees growing in the same block, these trees had an average yield of about 45 pounds per tree.

*Regularly of bearing.*—Considered regular and consistent.

TRUNK

*Size.*—Generally considered moderate. When measured at a distance of about 40 cm. above the ground height and when grown on 'Geisla 6' rootstock, the trunk had a diameter of about 7.5 cm.

*Bark texture.*—Considered smooth and typical for sweet cherry trees of a similar age.

*Bark color.*—Grey-Purple (RHS 187A).

*Lenticels.*—Generally — Considered numerous.

*Lenticels.*—Length — About 6.4 mm.; Width — 1.5 mm.

*Lenticels.*—Color — Grey-Orange (RHS 165A).

BRANCHES

*Surface texture.*—Considered smooth and typical for sweet cherry trees of the same age.

*Scaffold branches.*—Size — Considered medium for a 9 year old tree growing under similar circumstances. About 2.8 to about 4 cm. in diameter.

*Crotch angle.*—Generally — About 50 to about 90 degrees.

*Bark color.*—First year wood — Yellow-Green (RHS 146D).

*Bark color.*—Second year wood — Grey-Purple (RHS 187B).

*Bark color.*—Scaffold wood — Grey-Purple (RHS 186C).

*Branches.*—Lenticels — On first year wood, the lenticels have an average diameter of about 0.5 mm.

*Lenticels.*—Color — On first year wood, the lenticels have an orange-white color (RHS 159A).

*Lenticels.*—Second year wood — On average, the lenticels have a length dimension of about 1.5 mm. and width dimension of about 0.75 mm.

*Lenticels color.*—Second year wood — Considered White. This color is not distinctive of the variety.

*Scaffold wood.*—Generally — The scaffold wood appears to have approximately the same size and color characteristics as observed relative to the trunk bark noted, above.

LEAVES

*Leaf form.*—Considered oblong and having an acuminate tip.

*Leaf size.*—Length — Approximately 7.2 cm.; width — about 6.9 cm.

*Leaf color.*—Generally — Yellow-Green (RHS 147A).

*Leaf mid-vein.*—Considered large and about 1½ mm. in diameter.

*Leaf mid-vein color.*—The underside color is Green (RHS 142D).

*Leaf petiole.*—Average length — About 4.1 cm.

*Leaf surface texture.*—Considered glabrous.

*Leaf marginal form.*—Considered doubly serrate.

*Leaf glands.*—Numbers — Typically 2 leaf glands are found on each petiole and are located close to the blade end.

*Leaf glands.*—Size — About 2 mm. long, and about 1.2 mm. wide.

*Leaf gland.*—Color — At harvest maturity, the gland color is considered Red-Purple (RHS 61A).

*Leaf stipules.*—Generally — Are normally present, and average about 1 cm. in length.

FLOWERS

*Flower buds.*—Hardiness — Considered hardy under the ecological conditions prevailing near Orondo, Wash. This characteristic appears similar to the hardiness characteristic displayed by the 'Rainer' cherry trees growing at the same geographic location.

*Flower buds.*—Length — About 8.2 cm.

*Flower buds.*—Diameter — About 5.2 mm.

*Flower buds.*—Form — Considered plump and conical.

*Date of first bloom.*—About Apr. 10, 2006 under the ecological conditions prevailing near Orondo, Wash. As a general matter, the bloom produced by the 'MG 200' cherry tree was indistinguishable from that produced by the 'MG 200' cherry tree.

*Flowers.*—Size — When fully opened, the flowers have an average diameter of about 4.3 cm.

*Average bloom count.*—The present variety displays about 2.6 blooms per bud.

*Flower petals.*—Color — White. This color is not distinctive of the variety, however.

*Flower petals.*—Width — About 16.8 mm.

*Flower petals.*—Length — About 18.2 mm.

*Nectaries.*—Color — Yellow-Green (RHS N144B).

*Anthers.*—Size — Small and considered oval in shape. The average size of the anthers are about 0.75 mm. wide, and about 1 mm. in length.

*Anthers.*—Color — Orange (RHS N25D).

*Pollen production.*—Considered moderate.

*Pollen color.*—When mature, the pollen color is Yellow-Orange (RHS 19A).

*Pedicel.*—Average length — About 4.1 cm.

*Pedicel color.*—Yellow-Green (RHS 144D).

*Flower sepals.*—Form — Typically curled backwards towards the stem with the tips occasionally touching the pedicel.

*Flower pedicel.*—Color — Yellow-Green (RHS 143D).

FRUIT

*Maturity when described.*—Prior to the 2006 harvesting year, the date of harvesting of the 'MG 200' cherry tree was approximately the same time as the adjacent 'Rainer' cherry trees, that being an average date of about June 15, under the ecological conditions prevailing near Orondo, Wash. In the 2006 harvesting year, the cherries produced by the 'MG 200' cherry trees were harvested independently of the 'Rainer' cherry trees planted in the same block. The harvest date of 'MG 200' was about June 23$^{rd}$. In contrast, in 2006, the 'Rainer' cherry trees were harvested about June 27$^{th}$. On average, the present variety of cherry tree is ripe for harvesting and shipment about 4 days earlier than the 'Rainer' and 'Early Robin' cherry trees growing under substantially identical ecological conditions near Orondo, Wash.

*Size.*—Considered large to the species. As a general matter, the fruit size of 'MG 200' cherry tree average 1–1.5 row sizes larger than the fruit produced by the 'Rainer' cherry tree.

*Average diameter.*—Transverse in the suture plane in about 3.4 cm.

*Average diameter in the apical dimension.*—About 2.8 cm.

*Form.*—Generally — Considered uniform and having a short conical shape.

*Suture line.*—Present, but considered very shallow to wanting.

*Base shape.*—Considered rounded.

*Apex shape.*—Rounded to slightly indented.

*Fruit pressure.*—Generally — The following table of fruit pressures as measured in milligrams per millimeter were recorded at weekly storage intervals for the fruit produced by the 'MG 200', and 'Rainer' cherry trees in the one month following harvest in 2006.

| Date | Variety | Pressure m~/mm |
|---|---|---|
| Jun. 23, 2006 | MG 200 | 240.4 |
| Jun. 27, 2006 | Rainier | 273.7 |
| Jun. 30, 2006 | MG 200 | 254.8 |
| Jul. 3, 2006 | Rainier | 292.3 |
| Jul. 7, 2006 | MG 200 | 239.6 |
| Jul. 11, 2006 | Rainier | 272.4 |
| Jul. 14, 2006 | MG 200 | 247.5 |
| Jul. 18, 2006 | Rainier | 299.4 |
| Jul. 21, 2006 | MG 200 | 251.8 |
| Jul. 25, 2006 | Rainier | 289.2 |

*Stem.*—Average Length — About 4.4 cm.

*Stem.*—Color — Green (RHS 138A).

*Skin.*—Thickness — Considered medium for the species and not particularly distinctive of this variety.

*Surface texture.*—Glabrous.

*Tenacity to flesh.*—Considered tenacious.

*Tendency to crack.*—Yes. This characteristic is similar to the fruit produced by the 'Rainer' cherry trees under similar wet conditions.

*Down.*—Generally — Wanting.

*Skin color.*—Generally — Mature fruit coloring expressed by the 'MG 200' cherry tree covers a greater percentage of the surface area of the fruit and exhibits considerable difference in hue and chroma than that exhibited by the mature fruit produced by the 'Rainier' cherry trees and 'Early Robin' cherry trees as seen in the drawings. In this regard, the overcolor of the present variety is considered red (RHS 53B). The undercolor of the skin is yellow-orange (RHS 18B).

*Hue, chroma and brix comparisons.*—The following represents a comparison between the fruit produced by the 'MG 200'; 'Rainer'; and the 'Early Robin' cherry trees at harvest maturity at the same geographical location:

| Variety | Harvest Date | Average Hue | Average Chroma | Average Brix |
|---|---|---|---|---|
| MG 200 | Jun. 23, 2006 | 32.1 | 42.5 | 17.84 |
| Rainier | Jun. 27, 2006 | 55.5 | 37.5 | 15.28 |
| Early Robin | Jun. 27, 2006 | 76.8 | 37.5 | 16.72 |

*Flesh color.*—Yellow (RHS 2D).

*Pit cavity.*—Color — Yellow (RHS 2D).

*Flesh texture.*—Considered moderately firm and juicy. While the present variety is considered firm, the firmness of the fruit is not equal to that of the 'Rainer' cherry trees when grown under the same ecological conditions.

*Flesh fibers.*—Generally — Present. They are average and have no mouth feet.

*Date of ripening.*—About 4 days earlier than the 'Rainier' cherry trees at the same geographical location. In this regard, the present variety ripened for harvesting and shipment approximately Jun. 12, 2004; Jun. 15, 2005; and Jun. 25, 2006.

*Flesh flavor.*—Considered sweet and moderately low acid.

*Flesh Aroma.*—Considered slight.

*Eating quality.*—Considered excellent.

STONE

Figure 4:
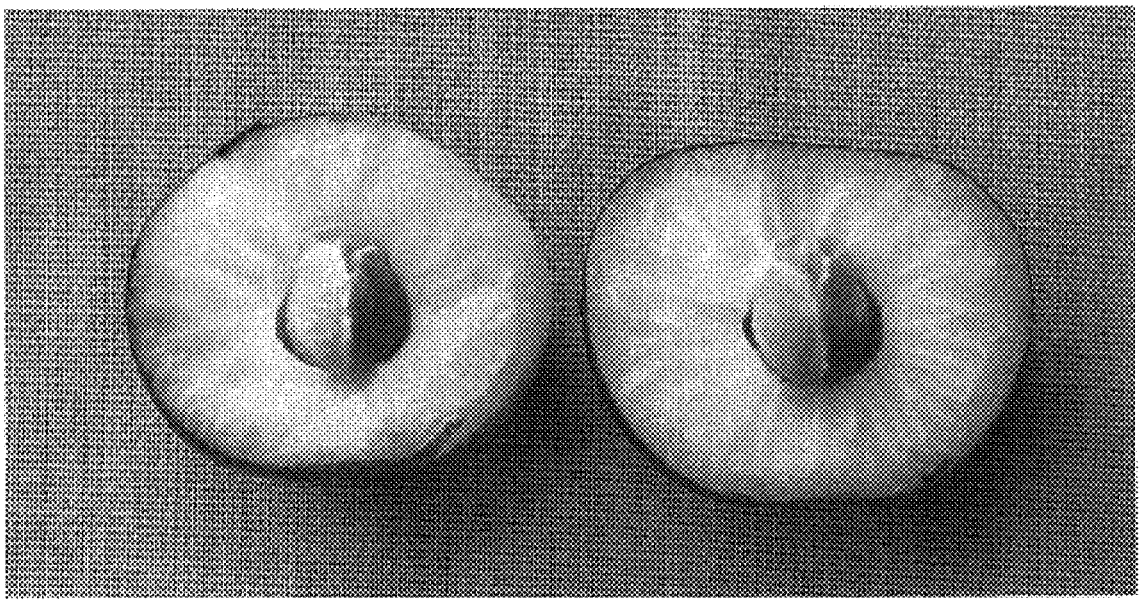
FIG. 4 depicts the nearly freestone characteristic of the cherries produced by the 'MG 200' cherry tree.

*Stone type.*—Considered nearly free-stone. In comparison, the stone of the 'Rainier' cherry trees are more adhering to the flesh. Still further, the fruit produced by the 'Early Robin' cherry tree exhibit a tight adherence of the flesh to the stone, and is therefore considered to be a cling-stone. Please see FIG. 4.

*Stone size.*—Considered medium for the species.

*Stone diameter.*—Approximately 12.8 mm. when measured from the apex to the base; 9.6 mm. when measured between the sutures; and about 7.7 mm. in diameter when measured between the sides.

*Stone form.*—Generally — Oval with one small wing protruding along the basal shoulder, and along the ventral suture. The small wing is located between two low ridges.

*Base.*—Shape — Slightly oblong.

*Helium.*—Shape — Slightly oblong.

*Apex.*—Shape — Rounded.

*Sides.*—Generally — They typically appear equal.

*Surface texture.*—Considered smooth.

*Ventral edge.*—Generally — About 1.5 mm. wide. The ventral edge is further subtended by two lower ridges which converge basally and apically. These narrow sutures average about 6 mm. wide at their mid-point.

*Dorsal edge.*—Generally — This feature appears as a sharp, smooth and slightly raised ridge which extends from the base to the apex.

*Stone color.*—Yellow-Orange (RHS 18D).

*Tendency of split.*—Not observed.

*Fruit use.*—Considered an early season cherry for premium fresh markets.

*Keeping quality.*—Generally considered excellent and equal to the fruit produced by the 'Rainer' cherry tree.

*Resistance to insects and diseases.*—No deficiencies noted. The present variety appears to have the same disease and insect resistance as that of the 'Rainer' cherry trees when grown under the ecological conditions common to Central Washington.

*Shipping quality.*—Considered very good and similar to that of the 'Rainier' cherry tree.

Although the new cherry tree possesses the described characteristics when grown under the conditions prevailing in Central Washington, it should be understood that variations of the usual magnitude and characteristics incident to changes in growing conditions, fertilization, pruning and pest control are to be expected.

Having thus described and illustrated my new variety of cherry tree, what I claim is new, and desired to secure by Plant Letters Patent is:

1. A new and distinct variety of cherry tree substantially as illustrated and described and which bears fruit having a red overcolor covering about 80% to 100% of the surface area, and a yellow-orange undercolor, and a mid-season date of ripening which is about 4 days earlier than the 'Rainier' and 'Early Robin' cherry trees when grown under the conditions prevailing in Central Washington.

* * * * *

UNITED STATES PATENT AND TRADEMARK OFFICE

CERTIFICATE OF CORRECTION

PATENT NO. : PP 18,825 P2
APPLICATION NO. : 11/599198
DATED : May 20, 2008
INVENTOR(S) : Marcus J. Griggs It is certified that error appears in the above-identified patent and that said Letters Patent is hereby corrected as shown below:

Column 1, line 20, replace “Rainer” with --Rainier--.

Column 2, lines 9; 14; and 24, replace all instances of “Rainer” with --Rainier--.

Figure 3:
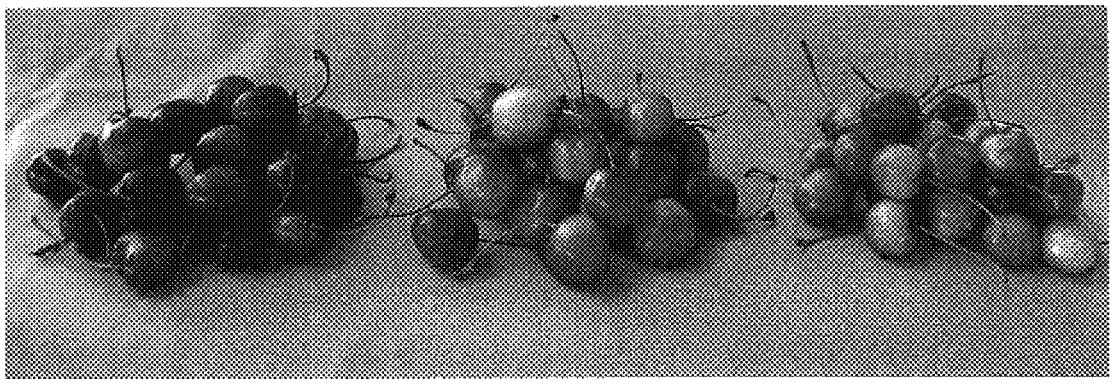
FIG. 3 depicts the mature fruit from the new variety 'MG 200' which is shown on the left of the photograph; fruit produced by 'Rainer' cherry trees (unpatented) in the center of the photograph; and the fruit produced by the 'Early Robin' cherry tree on the right of the photograph.

Column 3, Fig. 3, line 14, replace “Rainer” with --Rainier--.

Column 3, lines 38; 41; 50; 53; 58; and 63, replace all instances of “Rainer” with --Rainier--.

Column 5, lines 6; 45; 50; 52; 55; and 62, replace all instances of “Rainer” with --Rainier--.

Column 6, lines 10; 34; 49; and 66, replace all instances of “Rainer” with --Rainier--.

Column 7, line 2, replace “feet.” with --feel.--.

Column 8, lines 11 and 16, replace “Rainer” with --Rainier--.

Signed and Sealed this

Thirtieth Day of September, 2008

JON W. DUDAS
*Director of the United States Patent and Trademark Office*